(12) United States Patent
O'Keefe

(10) Patent No.: US 9,821,318 B2
(45) Date of Patent: Nov. 21, 2017

(54) SEPARATION OF ANALYTES

(75) Inventor: Donald O'Keefe, Doiylestown, PA (US)

(73) Assignee: Da Yu Enterprises, L.L.C., Doylestown, PA (US)

( * ) Notice: Subject to any disclaimer, the term of this patent is extended or adjusted under 35 U.S.C. 154(b) by 619 days.

(21) Appl. No.: 13/825,077

(22) PCT Filed: Sep. 23, 2011

(86) PCT No.: PCT/US2011/052917
§ 371 (c)(1),
(2), (4) Date: Mar. 19, 2013

(87) PCT Pub. No.: WO2012/040555
PCT Pub. Date: Mar. 29, 2012

(65) Prior Publication Data
US 2013/0180894 A1    Jul. 18, 2013

Related U.S. Application Data

(60) Provisional application No. 61/386,514, filed on Sep. 26, 2010.

(51) Int. Cl.
| | | |
|---|---|---|
| *B03B 5/52* | (2006.01) |
| *B01D 15/22* | (2006.01) |
| *B01D 15/34* | (2006.01) |
| *G01N 30/60* | (2006.01) |
| *B01J 20/281* | (2006.01) |

(52) U.S. Cl.
CPC ............... *B03B 5/52* (2013.01); *B01D 15/22* (2013.01); *B01D 15/34* (2013.01); *B01J 20/281* (2013.01); *G01N 30/6078* (2013.01); *G01N 30/6086* (2013.01); *B01J 2220/84* (2013.01); *G01N 30/6095* (2013.01)

(58) Field of Classification Search
CPC ....... B03B 5/52; B01J 20/281; B01J 2220/84; G01N 30/6078; G01N 30/6086; G01N 30/6095; B01D 15/34; B01D 15/22
See application file for complete search history.

(56) References Cited

U.S. PATENT DOCUMENTS

| | | | |
|---|---|---|---|
| 5,032,283 A | | 7/1991 | Scott |
| 5,716,852 A | * | 2/1998 | Yager .................... B01F 5/0403 366/DIG. 1 |
| 5,948,684 A | * | 9/1999 | Weigl .................... B01F 5/0403 422/81 |

(Continued)

FOREIGN PATENT DOCUMENTS

| | | |
|---|---|---|
| GB | 2423266 A | 8/2006 |
| WO | 9610170 A1 | 4/1996 |

(Continued)

*Primary Examiner* — Lore Jarrett
(74) *Attorney, Agent, or Firm* — Howson & Howson LLP

(57) ABSTRACT

A method and apparatus involving the configuration of an open capillary channel for size-based separation of analytes is described. The open capillary channel contains numerous turns of defined angles separated by intervening linear or curvilinear segments of capillary tubing. The configuration of the channel allows analyte differentiation based on diffusion coefficients and thus separates analytes by size.

7 Claims, 2 Drawing Sheets

(56) References Cited

U.S. PATENT DOCUMENTS

| | | | |
|---|---|---|---|
| 6,063,589 A * | 5/2000 | Kellogg | B01F 13/0059 366/DIG. 3 |
| 7,111,501 B2 | 9/2006 | Rocklin et al. | |
| 2004/0224425 A1 | 11/2004 | Gjerde | |
| 2006/0289059 A1* | 12/2006 | Krylov et al. | 137/7 |
| 2007/0059781 A1 | 3/2007 | Kapur et al. | |
| 2007/0122819 A1* | 5/2007 | Wu et al. | 435/6 |
| 2009/0255601 A1 | 10/2009 | Bauerle | |

FOREIGN PATENT DOCUMENTS

| | | |
|---|---|---|
| WO | WO9716724 A2 | 5/1997 |
| WO | WO9739338 A1 | 10/1997 |
| WO | WO9960397 A1 | 11/1999 |
| WO | WO2008130977 A2 | 10/2008 |

* cited by examiner

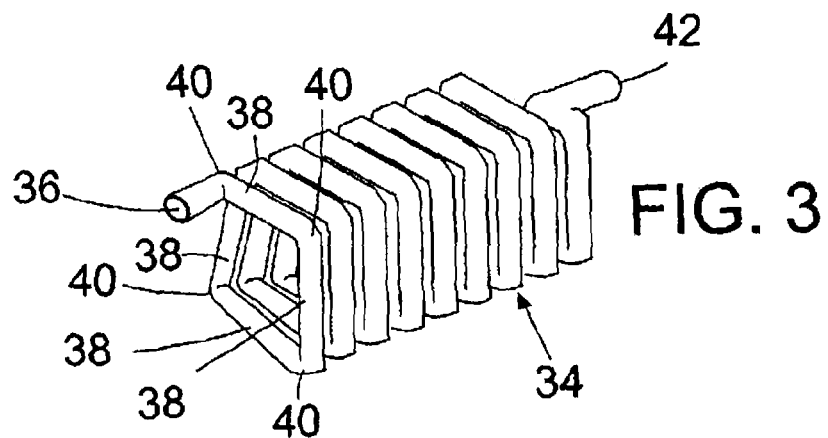
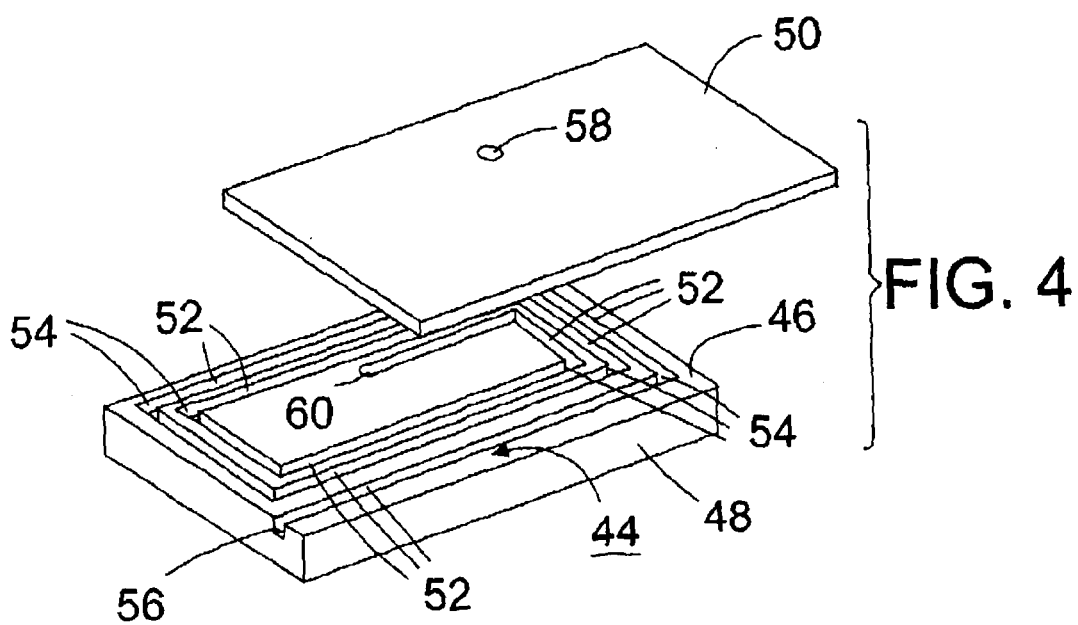

SEPARATION OF ANALYTES

FIELD OF THE INVENTION

This invention relates to an apparatus and process for separation of materials, and more particularly to instrumentation for carrying out size-based separation of analytes using high pressure liquid chromatography (HPLC).

BACKGROUND OF THE INVENTION

Chromatographic processes generally effect separation of a mixture into its components by dissolving the mixture in a mobile phase and passing the mobile phase over a stationary phase. Separation is achieved by differential partitioning of the components of the mixture between the mobile phase and the stationary phase. A mixture of analytes can be separated chromatographically into discrete subpopulations by utilizing intrinsic properties of the analytes, such as polarity, charge, function, and size.

Various chromatographic methods are known for size-based analyte separation. The most common method utilizes a steel column packed with a stationary phase consisting of spherical particles of silica or a polymer, with diameters typically in the range from approximately 4 to 17 microns. The spherical particles have pores of varying sizes. When the mobile phase passes over the particulate stationary phase, the entry of analytes into the pores depends on the sizes of the analytes as well as on the sizes of the pores. Smaller analytes enter more pores than larger analytes, and therefore tend to reside for a longer time within the column. Consequently, the concentration of larger analytes in the effluent of the column tends to be greatest at the beginning of the process while the concentration of smaller analytes in the effluent tends to become greatest later on in the process.

Size-based chromatographic methods include size-exclusion chromatography (SEC), gel filtration chromatography (GFC), and gel permeation chromatography (GPC). Although these methods are widely used, they are not without shortcomings.

A first drawback is that the particulate stationary phase in a chromatographic column can act as a filter. Some large analytes may not pass through the column at all, and therefore go undetected.

A second drawback is that separations utilizing chromatographic columns tend to be slow. Separation and column re-equilibration often take 60 minutes or more. In theory, separation time can be decreased by increasing the flow rate of the mobile phase. However, at best, the separation time can be decreased only by a modest amount because increasing the flow rate increases the pressure on the stationary phase and the increased pressure can crush the porous particles, destroying the column's capacity for separation.

A third drawback is that the particles in a silica-based stationary phase begin to dissolve when exposed to a liquid having an alkaline pH (i.e., a pH greater than 8). On the other hand, although polymeric-based stationary phases can readily accommodate a greater pH range, some analytes can be absorbed by polymeric-based particles. The mutual affinity for some analytes and polymeric particles introduces an additional differentiating property into the separation process, and the process becomes a mixed mode process, no longer based exclusively on the size of the analyte.

Capillary Hydrodynamic Fractionation (CHF) is another sized-based separation technique. In CHF, liquid flows through a long, narrow capillary tube. The velocity profile of the flow through the capillary is approximately parabolic (Poiseuille flow). The velocity of the liquid is greatest at the center of the capillary, and decreases toward the capillary wall, where it becomes almost stagnant. Analytes injected into the capillary spread through the capillary's bore and experience all possible flow rates. At any given moment, an analyte particle migrates at the flow rate closest to its hydrodynamic center. The closest approach of the hydrodynamic center of an analyte particle to the capillary wall is approximately equal to the particle's hydrodynamic radius. Smaller analytes can therefore approach the capillary wall more closely than the larger analytes, and their movement, when closer to the capillary wall, is influenced by the lower liquid flow rates adjacent the capillary wall. The result is that larger analytes remain in the vicinity of the higher flow rates in the capillary and have a higher mean velocity than smaller analytes. The larger analytes are therefore eluted first, and separated from smaller analytes.

The absence of a particulate stationary phase in CHF is advantageous because fast separation times (e.g., 7-10 minutes) can be achieved. However, the CHF technique has poor resolution and is primarily applicable in the separation of colloids. In addition, the very narrow capillary bore (typically having a diameter in the range from approximately 1 to approximately 10 microns) makes detection of the analytes difficult.

CHF has not found significant application in the separation of biological molecules such as proteins, which often have sizes less than the typical separation range of approximately 0.015 to 1 micron in CHF.

Hydrodynamic chromatography (HDC) is a size-based separation technique that includes elements of both GPC and CHF. HDC utilizes a tubular column containing a particulate stationary phase as in GPC. However, unlike the stationary phase particles in GPC, the particulate stationary phase in HDC is non-porous. The nonporous particles form a network of interstitial spaces accessible by the liquid mobile phase. The interstitial spaces are intended to approximate the long capillary tube found in CHF. As in CHF, analytes are separated in HDC on the basis of their mean velocity due to the Poiseuille flow along the walls of the column and along the surfaces of the nonporous particles that form the interstitial spaces.

The typical separation range for HDC is approximately 0.01-10 microns, and has limited the technique mostly to the analysis of submicron colloidal particles. HDC suffers from many of the same shortcomings as GPC, including long analysis times and potential column damage due to high pressures.

Flow field-flow fractionation (FFF) is a sizing technique applicable to both biological molecules (e.g., proteins) and colloids. The fractionation device consists of a separation channel approximately 10-50 centimeters long, 1-3 centimeters wide and 0.01-0.05 centimeters thick. The channel is bounded by an upper wall and a lower wall, the latter referred to as an "accumulation wall." The upper wall is formed by a permeable membrane, and the lower wall is porous and covered by a filter that serves as a barrier to analytes. During the separation process, liquid flows lengthwise in the channel in laminar flow, with a parabolic velocity profile similar to that found in CHF. Simultaneously, flow perpendicular to the length of the channel emanates from the membrane forming the upper wall, creating a convective flux. Liquid exits the channel both through the accumulation wall, and through the distal end of the channel where an analyte detector is located. The convective flux resulting from the perpendicular cross flow in the channel promotes separation of analytes based on differences in their diffusion coefficients. An analyte's diffusion coefficient is inversely related to its size as defined by the Stokes-Einstein equation. $D=k_BT/6\pi\eta r$, where D is the analyte's diffusion coefficient, $k_B$ is Boltzmann's Constant, T is the absolute temperature, n is the dynamic viscosity of the liquid, and r is the analyte's hydrodynamic radius (i.e., the analyte's size). Separations based on an analyte's diffusion coefficient are therefore similar to separations based on size.

During FFF separation, the cross flow drives analytes toward the accumulation wall, and the analyte concentration increases with decreasing distance from the accumulation wall. This creates an analyte concentration gradient that triggers the analyte's diffusion away from the accumulation wall and toward the center of the channel, where the flow rate is greatest because of the parabolic flow profile. Therefore, analytes with higher diffusion coefficients (i.e., smaller sizes) will diffuse into areas within the channel where the flow rate is greatest, and will elute earlier than larger analytes. This explanation for FFF separation is valid for biological macromolecules and submicron particles, but is not applicable to larger micron-sized particles.

FFF is a relatively new methodology for size-based separations, especially for the separation of biological macromolecules. However, FFF applications for size-based separations have not attained wide usage due to the requirement for specialized and expensive equipment. Additionally, FFF separations are relatively slow, often requiring an hour or more for completion.

Several known electrophoretic methods are capable of separating analytes based on their size. These methods include gel electrophoresis and capillary electrophoresis.

Gel electrophoresis utilizes an electric field to mobilize analytes through a semisolid medium, most often composed of polyacrylamide or agarose. Gel electrophoretic methods for sizing have mostly been applied to biological molecules such as proteins and nucleic acids. These methods are ubiquitous, but they have several drawbacks. First, analytes are often pre-treated under harsh conditions prior to analysis. In many cases, pre-treatment alters the analytes' structure and size, creating inaccuracies in sizing results. Second, gel electrophoresis is relatively labor intensive. Third, analysis times are lengthy, often in excess of two hours. Fourth, sample throughput is low. Generally only 5-10 samples can be analyzed in a single gel.

Capillary electrophoresis (CE) is an alternative to gel electrophoresis. CE sizing techniques utilize a narrow-bore capillary containing a polymer solution acting as a sieving matrix to which an electric field is applied. Although CE offers a potential for higher sample throughput and faster analysis times than gel electrophoresis, some sizing results in CE are inaccurate due to destructive pretreatment of samples, notably proteins.

Analytical ultracentrifugation (AUC) is a non-chromatographic method that separates analytes of different sizes based on their sedimentation velocity when rotated in a centrifuge. AUC is a low throughput technique, often only able to process a few samples at a time. Each analysis requires several hours. AUC is also a highly specialized technique requiring significant user training prior to routine use.

SUMMARY OF THE INVENTION

This invention is a method and apparatus for separating analytes rapidly and effectively based on their size.

The apparatus in accordance with the invention comprises a liquid reservoir, an analyte detector, a pump arranged to transfer liquid from the reservoir, through a liquid path to the analyte detector, and a port for injection of a sample into the liquid path, all conventional components. The apparatus is characterized by a specially formed capillary channel, constituting at least a part of the liquid path downstream of the injection port. The capillary channel comprises a series of elongated segments, each said segment having a smooth linear or curvilinear shape, in which flow of liquid containing a sample injected through the injection port can take place. The elongated segments of each successive pair of elongated segments in the series extend in different directions, and are connected to each other through a bend in the liquid path sufficiently sharp to induce a non-laminar flow or a convective flow of liquid in the vicinity of the bend. Each of the elongated segments has an upstream end and a downstream end, and is sufficiently long to allow non-laminar flow at its upstream end to dissipate and laminar flow to reestablish at a location between its upstream and downstream ends.

In some preferred embodiments, the capillary channel comprises an elongated tube composed of a series of elongated segments connected to one another by abrupt bends. The elongated tube can be formed into a helix composed of turns having substantially rectangular projections.

In other preferred embodiments, the capillary channel is disposed with its center line substantially in a plane. These embodiments can be made by etching a channel in the surface of a first plate or microchip and covering the channel by means of a cover in facing relationship to the etched surface. Preferably, the channel is in the form of a spiral comprising a series of elongated segments connected by abrupt bends.

Another aspect of the invention is a method for separation of analytes based on size. The method comprises pumping, through an elongated, capillary liquid path, a liquid containing a sample including at least two different analytes having different sizes, and establishing, in the capillary liquid path, alternating regions of non-laminar and laminar flow, whereby separation of the analytes is enhanced because the smaller analytes, having higher diffusion coefficients, tend to aggregate in central parts of the non-laminar regions, and pass into the more rapidly flowing central region of the fluid stream when laminar flow is reestablished.

The regions of non-laminar flow are preferably established by abrupt changes in the direction of flow of the sample-containing liquid. The regions of laminar flow are preferably established in smoothly curving or straight segments of the elongated capillary liquid path.

The flow rate of the liquid containing a sample is preferably controlled to allow laminar flow to take place along a major part of the length of each smoothly curving or straight segment.

BRIEF DESCRIPTION OF THE DRAWINGS

FIG. 3 is a diagrammatic perspective view of a capillary channel according to a first embodiment of the invention; and FIG. 4 is a diagrammatic perspective view of a capillary channel according to a second embodiment of the invention.

DETAILED DESCRIPTION OF THE PREFERRED EMBODIMENTS

The separating apparatus according to the invention utilizes an open capillary channel, i.e., one not containing a particulate medium. The open capillary channel comprised a plurality of linear or curvilinear segments connected by angular bends. In an embodiment of the invention, the channel can be formed by a capillary tube composed of stainless steel or a polymeric resin, for example a poly(aryl-ether-ether-ketone) resin known as "PEEK," e.g., poly(oxy-1,4-phenylene-oxy-1,4-phenylene-carbonyl-1,4-phenylene). In another embodiment, the capillary channel can be etched on the surface of a plate or chip and completed by applying a cover to the plate or chip.

Figure 1:
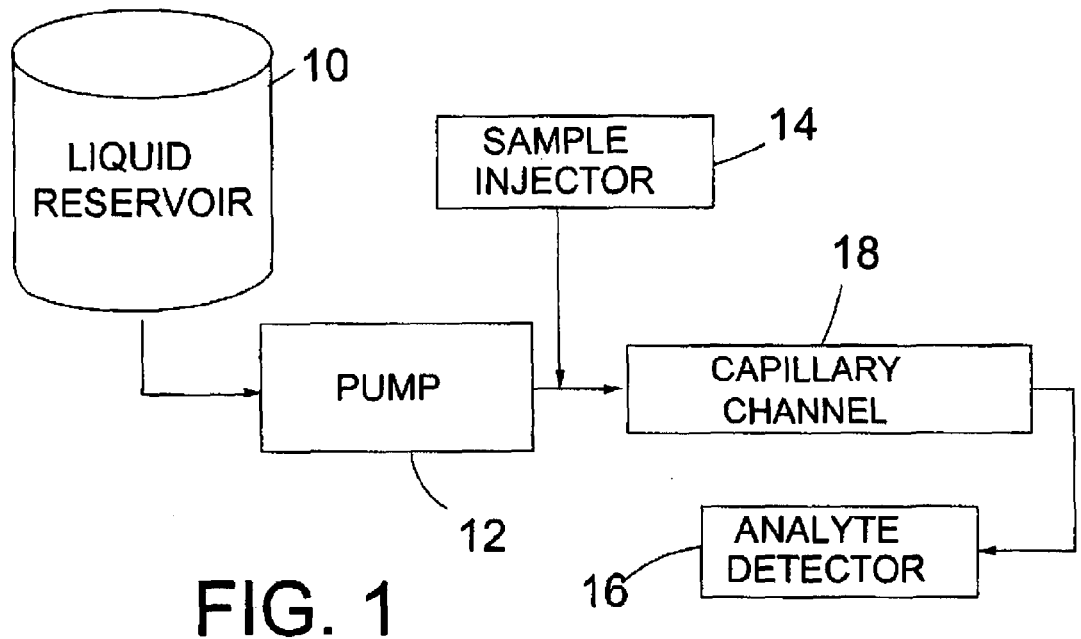
FIG. 1 is a schematic diagram showing an apparatus for chromatographic separation of analytes in accordance with the invention.

As shown in FIG. 1, the basic apparatus according to the invention is composed of a liquid reservoir 10, a conventional liquid chromatograph pump 12, a conventional sample injector 14, conventional analyte detection apparatus 16, and a specially constructed capillary channel 18. The capillary channel can take any of various forms, but in each case, it comprises a series of elongated segments, each having a smooth linear or curvilinear shape, connected to one another by bends sufficiently sharp to induce non-laminar flow in the flow of liquid in the vicinity of the bends. The term "non-laminar" flow as used herein refers to turbulent flow, or transient flow, i.e., flow that takes place in the transition between laminar and turbulent flow. Each segment should be sufficiently long to allow non-laminar flow at its upstream end to dissipate, and laminar flow to reestablish at a location between its upstream and downstream ends. Preferably laminar flow should be reestablished in each segment at a location closer to the inlet end than to the outlet end so that laminar flow exists in a major portion of the length of each segment.

Analyte separation in the apparatus and method of this invention is based on diffusion principles. As in the flow field-flow fractionation (FFF) technique, the analyte's diffusion coefficient is inversely related to its size as defined by the Stokes-Einstein equation. $D=k_B T/6B\pi r$. Simply stated, small analytes have greater diffusivity because they have higher diffusion coefficients.

Figure 2:
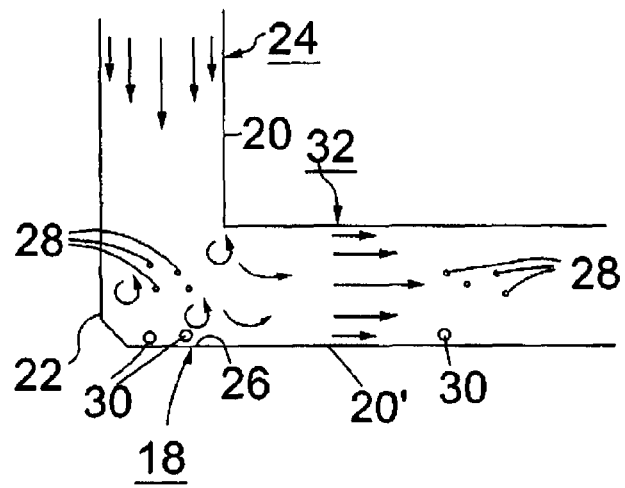
FIG. 2 is a schematic diagram illustrating the effects of diffusion and laminar flow in the separation of analytes of different sizes.

FIG. 2 depicts a portion of the capillary channel 18 of FIG. 1 in which laminar flow of a mixture of analytes in a carrier liquid takes place in a smooth, straight, channel segment 20 as depicted by arrows 24. The lengths of the arrows indicate the approximately parabolic velocity profile within the channel. The rate of flow in the central part of the channel is highest, and gradually decreases toward the side walls of the channel.

At the bend 22, which is a 90° bend in the embodiment shown, the flow becomes non-laminar. The flow of liquid into the bent portion of the channel, exerts a vector force that causes the analytes in the bent portion to concentrate against the external wall 26 of the channel. However, the force exerted on the analytes by the flow of liquid in channel segment 20 is opposed by the analytes' diffusion and by the force exerted by the flow leading out of bend 22 into straight segment 20'.

Smaller analytes 28, which have higher diffusion coefficients, more strongly oppose the force exerted by the flow of liquid toward the bend, and therefore migrate farther away from the external wall 26 of the capillary toward the center of the capillary channel. The larger analytes 30, on the other hand, which have lower diffusion coefficients, tend to remain closer to the external wall 26. As a result, as the carrier liquid and analytes exit the bend and proceed into segment 20', the larger analytes 30 are concentrated near the channel wall while the smaller analytes 28 are concentrated in the central part of the channel.

Within a short distance from the bend, laminar flow, as depicted by arrows 32, is reestablished. Since, under the laminar flow condition in the segment 20', the flow velocity is greatest in the center of the capillary and approaches zero near the capillary walls, the smaller analytes 28 exiting the bend 22 of the will attain greater velocity within the segment 20' than the larger analytes 30.

As the analytes enter the second angular portion of the capillary, the process is repeated, and increased separation of the smaller analytes from the larger analytes takes place. Continued flow through the additional bends and intervening straight or smoothly curved segments of the capillary channel 18 results in increased separation of the smaller analytes having high diffusion coefficients from the larger analytes having lower diffusion coefficients.

The capillary channel preferably contains a large number of alternating straight or smoothly curved segments and sharp bends. For efficient use of space, the channel can be a tubular channel in the form of a helix in which an axial projection of each turn is substantially rectangular in shape. An example of a rectangular helical tube is the tube 34 shown in FIG. 3, which has and inlet opening 36, substantially straight segments 38, 90° bends 40, and an outlet opening 42.

The rectangular turns can be stacked closely for optimum use of space. The rectangular/helical tube 34 is ideally suited for use in existing chromatographic equipment, and the inlet and outlet openings of the tube can be provided with suitable fittings (not shown) for attachment to conventional chromatography equipment.

An alternative version of the channel according to the invention can be produced by etching an open channel in a plate or microchip as shown in FIG. 4. A channel 44, having a rectangular transverse cross-section, is formed by etching, machining, or another suitable process, in surface 46 of a plate 48, and covered by another plate 50. The channel consists of a series of elongated segments 52 connected by bends 54. An inlet opening 56 is formed along an edge of plate 48, and an outlet opening 58 is formed in plate 50 at a location at which it registers with end 60 of channel 44. The channel is substantially in the form of a spiral made up of straight elongated sections connected by sharp right angle bends. The centerline of the channel, that is, a line extending lengthwise within the center of the cross-section of the channel lies substantially in a plane. The function of the channel 44 is the same as that of channel 18 in FIG. 1 and the channel in tube 34 of FIG. 3.

If the flowing liquid is used as a frame of reference, the bends, except for those at the ends of the channel, all turn in the same direction both in the rectangular helix configuration of FIG. 3 and in the planar spiral configuration of FIG. 4. That is, from the point of view of an analyte molecule moving along with the liquid in the capillary channel, all of the turns are "left" turns or all of the turns are "right" turns. Having substantially all of the turns, or at least the majority of them, in the same direction helps to keep the larger analyte molecules on the same side of the channel, resulting in more effective separation of the smaller analyte molecules from the larger ones.

Some advantages of the invention can be realized with other channel configurations. For example, a planar channel version can be formed of alternating smoothly curved U-shaped segments and straight segments connected to one another by sharp bends. Various non-planar configurations for etched channels can also be utilized.

Advantages of the invention can also be realized in numerous other variations of the embodiments described above. For example, the angles of the bends do not need to be 90° angles. Nor do all of the angles need to be equal. It is only necessary for the angles to be sufficiently sharp to produce non-laminar flow regions in the carrier liquid in the channel. Similarly, the lengths of the straight or smoothly curved channel segments can vary and do not need to be equal. It is only necessary for the lengths of the channel segments to be sufficient for the reestablishment of laminar flow at some intermediate point between successive bends. The overall length of the capillary channel and the total number of angular bends and intervening straight or smoothly curved segments can vary over a wide range.

The internal diameter of the capillary channel should be such as to allow laminar flow in the straight or smoothly curved portions of the apparatus. Generally, laminar flow is defined by a Reynolds number less than 2300. The Reynolds number (Re) is defined as $Re=\rho QD_h/nA$ where $\rho$ is the density, Q is the volumetric flow rate, $D_h$ is the hydraulic (internal) diameter, A is the cross-sectional area, and n is the dynamic viscosity. Preferably the internal diameter of the capillary channel, if circular, is less than 2 mm.

The lengths of the intervening straight or smoothly curved segments must be sufficient to allow the re-establishment of laminar flow. The length before laminar flow is re-established in a capillary tube is referred to as the entrance length ($L_e$), where $L_e=0.06Re(D_h)$ for laminar flow. It is desirable in the present invention that the lengths of the intervening straight or smoothly curved segments be at least one and a half times the entrance length.

There are several variables that must be established to effect a specific separation. Conditions that effectively separate a 10,000 dalton molecule from a 100,000 dalton molecule may not be effective for separating a 300,000 dalton molecule from a 1,000,000 dalton molecule. Thus, variables must be established empirically. Variables for the apparatus include the number of angular portions, the magnitude of those angles, the number of intervening segments, and the lengths of those segments. Process variables include the flow rate, the composition of the carrier fluid and the temperature of the fluid. The flow rate must be low enough to allow laminar flow in the intervening straight or smoothly curved segments. The composition of the carrier fluid is important because its viscosity has an impact on the diffusion coefficients of the analytes. Furthermore, including additives such as polyethylene glycol, ficoll, or other related compounds into the fluid can further effect separation due to molecular crowding. The fluid temperature also effects separation directly by impacting the analytes' diffusion coefficients, and indirectly by changing the carrier fluid viscosity.

The invention claimed is:

1. A method for separation of analytes based on size, the method comprising:
   pumping a liquid containing analytes of at least two different sizes through an elongated, open, capillary liquid path defined by a capillary channel wall, said capillary liquid path comprising a plurality of elongated segments and a plurality of bends, the elongated segments being connected to one another in a series by said bends, each said elongated segment having a smooth linear or curvilinear shape; and
   establishing, by abrupt changes in the direction of flow of said liquid at said bends, alternating regions of non-laminar and laminar flow;
   causing larger analytes to concentrate nearer than smaller analytes to said capillary channel wall, and causing smaller analytes to concentrate nearer than larger analytes to a central portion of the capillary liquid path; and
   controlling the rate of flow of said liquid through said capillary liquid path to allow laminar flow to take place along a part of the length of each said elongated segment, whereby said smaller analytes travel faster than said larger analytes through said elongated segments and are thereby separated from said larger analytes.

2. The method according to claim 1, in which the steps of pumping a liquid containing analytes, establishing alternating regions of non-laminar and laminar flow, causing larger analytes to concentrate nearer than said smaller analytes to the capillary channel wall, causing smaller analytes to concentrate nearer than larger analytes to a central portion of the capillary liquid path, and controlling the flow rate of said liquid, are carried out using an apparatus comprising:
   a liquid reservoir;
   an analyte detector;
   a pump arranged to transfer liquid from the reservoir, through said elongated, open, capillary liquid path to the analyte detector, said analyte detector being located downstream of said liquid path; and
   a port for injection of a sample containing said analytes into said liquid path; and
   in which the elongated segments of each pair of successive elongated segments in said series extend in different directions and are connected to each other through one of said bends, each of said bends in said path being sufficiently sharp to induce non-laminar flow of liquid in its vicinity when the rate of flow of said liquid through said capillary liquid path is controlled to allow laminar flow to take place along said part of the length of each said elongated segment; and
   in which each of said elongated segments has an upstream end and a downstream end and is sufficiently long that non-laminar flow at its upstream end dissipates, and laminar flow is reestablished, at a location between its upstream and downstream ends.

3. The method according to claim 2, in which the capillary liquid path has a center line disposed substantially in a plane.

4. The method according to claim 2, in which said capillary liquid path has a center line disposed substantially in a plane, and is in the form of a spiral comprising a series of elongated segments connected by said bends.

5. The method according to claim 2, in which said capillary liquid path comprises an elongated tube formed into a helix composed of substantially rectangular loops.

6. The method according to claim 2, in which said capillary liquid path is formed by an elongated depression in the surface of a first plate, and a cover in facing relationship to said surface.

7. The method according to claim 2, in which each of said elongated segments is sufficiently long that non-laminar flow at its upstream end dissipates, and laminar flow is reestablished, at a location closer to its upstream end than to its downstream end.

* * * * *

UNITED STATES PATENT AND TRADEMARK OFFICE
CERTIFICATE OF CORRECTION

| | |
|---|---|
| PATENT NO. | : 9,821,318 B2 |
| APPLICATION NO. | : 13/825077 |
| DATED | : November 21, 2017 |
| INVENTOR(S) | : Donald O'Keefe |

It is certified that error appears in the above-identified patent and that said Letters Patent is hereby corrected as shown below:

In item "(75) Inventor", "Doiylestown," should read --Doylestown,--.

Signed and Sealed this
Eighth Day of May, 2018

Andrei Iancu
*Director of the United States Patent and Trademark Office*